United States Patent [19]
Strobl et al.

[11] Patent Number: 5,751,340
[45] Date of Patent: May 12, 1998

[54] METHOD AND APPARATUS FOR REDUCING THE INHERENTLY DARK GRID PATTERN FROM THE VIDEO DISPLAY OF IMAGES FROM FIBER OPTIC BUNDLES

[75] Inventors: Karlheinz Strobl, Fiskdale, Mass.; Bryan D. Kennedy; David Chatenever, both of Santa Barbara, Calif.; Klaus Irion, Tuttlingen, Germany

[73] Assignee: Karl Storz GmbH & Co., Tuttlingen, Germany

[21] Appl. No.: 701,131

[22] Filed: Aug. 21, 1996

[51] Int. Cl.$^6$ ............................ A61B 1/04; H04N 5/21; H04N 5/235
[52] U.S. Cl. ................................ 348/65; 348/615
[58] Field of Search .................... 348/65, 73, 607, 348/615; H04N 5/21, 5/235

[56] References Cited

U.S. PATENT DOCUMENTS

| | | | |
|---|---|---|---|
| 4,480,636 | 11/1984 | Karaki | 348/65 |
| 4,633,303 | 12/1986 | Nagasaki | 348/65 |

Primary Examiner—Howard W. Britton
Attorney, Agent, or Firm—Donald D. Mon

[57] ABSTRACT

A method and apparatus for improving an image received from a endoscope having a flexible fiber optic bundle that produces an interstitial grid overlay due to the dead space between each fiber pixel. The interstitial grid pattern in the image, is substantially eliminated by processing the image through a linear digital filter to attenuate the first-order spatial frequency components that contribute most to the interstitial pattern. The filter employs relatively small convolution kernels that are optimized for specific fiber spacing. The image is then processed through the linear digital filter by convolving the respective pixels in the image by the derived coefficients. The image is improved and the grid pattern may also be reduced by a dilation process which involves processing the image through a dilation algorithm to "grow" the bright center of each fiber pixel in the image so that the effect of the grid pattern is reduced. The process involves filling in the dark area of the grid space with the color and intensity from the nearest fiber center to obtain an equivalent image representation. The dilation process uses a non-linear image processing algorithm to replace each pixel with the maximum pixel brightness in its immediate neighborhood depending on the selection of a kernel. The dilation kernel is selected by determining the number of detector (CCD) pixels that fit in a space between the fiber cores and then selecting a matrix size and kernel pattern.

27 Claims, 7 Drawing Sheets

METHOD AND APPARATUS FOR REDUCING THE INHERENTLY DARK GRID PATTERN FROM THE VIDEO DISPLAY OF IMAGES FROM FIBER OPTIC BUNDLES

FIELD OF THE INVENTION

This invention relates to endoscope image improvements and more particularly relates to the reduction of the grid pattern which inherently exists in images obtained through endoscope fiber optic bundles, in video displays of the images.

BACKGROUND OF THE INVENTION

Endoscopes which utilize lenses for relaying an image from its distal end provide a continuous image without interstitial voids. These optical systems are most frequently used in rigid endoscopes.

For many types of endoscopes, especially but not exclusively for flexible endoscopes, rigid relay lens or portions of the image conducting elements are less useful, and fiber optic bundles are used instead. These bundles comprise thousands (e.g. 10,000–30,000) of very small cylindrical fibers that are carefully aligned in a parallel array. Each fiber carries a portion of the image (fiber and pixel) and the image itself is viewed as an assemblage of these portions.

Each fiber consists of a light transmitting core, and a peripheral cladding which will consist of one layer or more frequently of two layers for fully flexible bundles. Light for an image is not transmitted through the cladding for typical fiber lengths.

These fibers nest relative to one another so as to array the fibers in hexagonal, or quasi-hexagonal patterns. Between each group of three neighboring fibers there is a void space which has generally a triangular like shape. Light for an image is not transmitted through these voids. The combined cladding and void regions form an "interstitial region" in the form of a visible grid.

As a consequence, the light-conveying fibers are embedded in a grid through which light is not transmitted. This grid forms a generally hexagonal pattern. The image formed at the proximal end of the fiber bundle therefore comprises a pattern of information-containing regions at the ends of the cores, and a dark grid of the interstitial region around them where the claddings and voids are located.

These bundles in order to be used in an endoscope must be very small, and the image must be substantially magnified. When it is magnified, the grid becomes evident to the surgeon, who often finds it to be a distraction.

The images from the fibers are projected onto a camera, such as a CCD, which generates in pixel form a signal respective to the lighted areas of the cores, and to the dark grid pattern. In turn, this signal is transmitted to a large video display which is observed by the surgeon while he performs the operation. Direct viewing through an endoscope is becoming less frequent, as surgeons become accustomed to remote manipulation while watching a relatively large video screen. For this reason, the dark grid pattern becomes even more evident to the surgeon.

As a consequence of the grid reduction, a better and more agreeable visual image is produced. It is brighter, in large part due to the reduction (or near elimination) of the dark grid. It can readily be magnified without showing overbearing grid effects.

As the diameter of the core decreases, the relative proportion of grid increases, because the thickness of the cladding is approximately the same regardless of the diameter of the core. With the use of this invention, fiber optic bundles with a disagreeably larger grid pattern, can be used and also bundles in less than perfect condition.

Present real-time image processing involves contrast enhancement, image averaging, smoothing, image rotation, warping, etc. However, this real-time image processing is typically a global process and not sensitive to local image defects of a flexible endoscopic system. Defects such as the interstitial fiber grid pattern are not eliminated without also reducing the information content (resolution) which an observer can distinguish in such electronically produced images. The interstitial fiber grid pattern in the image can interfere with the image much like observing an image through a screen. While the human eye can view the image through the screen (i.e., interstitial grid pattern) it interferes with the information content of the image.

Endoscopes, having flexible coherent image fiber bundles to transmit a pixilated image from a digital objective lens group to an objective lens group, generally have a lower image quality due to the lower fiber count of the image bundles in relationship to the pixel count on the CCD and the image has a grid overlay due to the dead space (grid) between each fiber pixel. This image defect reduces the overall brightness of the image, limits the maximum visible acceptable image magnification, and distracts the observer.

The above and other novel features of the invention will be more fully understood from the following detailed description and the accompanying drawings, in which:

BRIEF DESCRIPTION OF THE DRAWINGS

This invention is accomplished in combination with an endoscope having an image-forwarding fiber optic bundle. The bundle itself typically comprises a laid array of circularly-sectioned fibers which nest together. Each fiber consists of a light- forwarding core, and a peripheral cladding which does not forward light. A void is left between each set of three fibers which also does not forward light. It is this assemblage of claddings and voids that creates a dark grid in which the information-bearing cores are embedded.

The image from the distal end of this bundle is applied to a CCD camera which produces a signal with pixels respective to all areas of the image, cores and grid pattern together.

Figure 1:
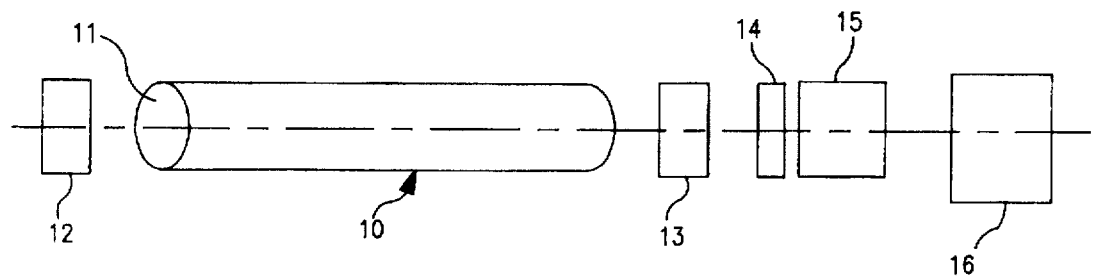

According to this invention, the raw signal from the CCD is processed to produce a compensated signal in which the grid pattern is at least reduced in prominence, by providing to the video screen a compensated image in which this grid pattern area is caused to be presented so as to contrast less sharply with the color or intensity of its adjacent cores.

According to yet another optional feature of the invention, the compensated signal respective to the areas of the grid pattern is derived through a linear filter. In the spatial domain the filter's impulse response is convolved with the sampled fiber scope image. In the spatial-frequency domain the fiberscope spectrum is multiplied by the filter's frequency response.

The interstitial grid pattern is substantially eliminated by processing the endoscope image through a linear digital filter. The filter is designed by employing relatively small kernels having elements that are optimized for a specific fiber spacing. In the preferred embodiment, a 3×7 element kernel is selected and the coefficients for each element are calculated. That is, a typical filtering kernel measures three elements vertically by seven elements horizontally and has a total of twenty-one elements. The kernel is then employed in a convolution process given by the following equation:

$$g_{i,j} = \sum_{l=-N}^{N} \sum_{k=-M}^{M} h_{i-l,j-k} f_{k,l}$$

where $f_{i,j}$ and $g_{i,j}$ denote pixels in the input and output images of the convolution process, respectively, and integers i and j are horizontal and vertical indices. The convolution kernel has horizontal and vertical dimensions 2M+1 and 2N+1, respectively, and has elements denoted by $h_{i,j}$. For the 3(V)×7(H) kernel, M and N have values 3 and 1, respectively. The combination of kernel and convolution processing produces a filtered output that has a substantially attenuated interstitial grid pattern.

According to one optimal feature of the invention, the area of the pattern can be reduced in size by dilating the displayed areas of the core images. The dilation process involves expanding or "growing" the bright center of each fiber pixel in the image so that the interstitial grid pattern is reduced. This dilation process increases the brightness without losing any real information, and the visual distraction of the grid is reduced. The dilation process involves filling the grid space between respective pixels in the image to increase the average image brightness to obtain an image constant image peak intensity, which substantially eliminates the grid pattern. This method involves discarding non-useful information (i.e., the dark area of the grid pattern) and replacing it with useful information such as the brightness of nearby fiber pixels.

An important advantage of both the convolution and processes is that the image brightness can be increased without requiring a brighter light source, thereby minimizing the potential heat generation at the tip of the endoscope when it accidentally comes into contact with absorbing tissue. This allows the endoscope user to significantly increase the image brightness. The image transformation, by dilation or convolution processing can be made in real-time.

The dilation process involves selecting a kernel based on fiber spacing, and then processing the image through the algorithm in the image processing chip. The kernel chosen depends upon the image magnification and fiber to fiber spacing, and fiber core spacing ratio. Each pixel is replaced with the maximum pixel brightness of another pixel in its immediate neighborhood, depending upon the kernel chosen by processing the image through a non-linear image processing algorithm. Processing the image through the dilation algorithm reduces the grid pattern so that visually, one can see more detail in the image due to less interference from the grid pattern.

A secondary process such as a second dilation using the same or different kernel, or using the linear digital low pass filtering described hereinabove, or smoothing or any combination thereof may be used to further improve the image appearance depending upon the type of information viewed.

The above and other features of this invention will be fully understood from the following detailed description and the accompanying drawings, in which:

DETAILED DESCRIPTION OF THE DRAWINGS

FIG. 1 is a diagram of endoscope coupled to a charge coupled device (CCD) through lenses.

Figure 2:
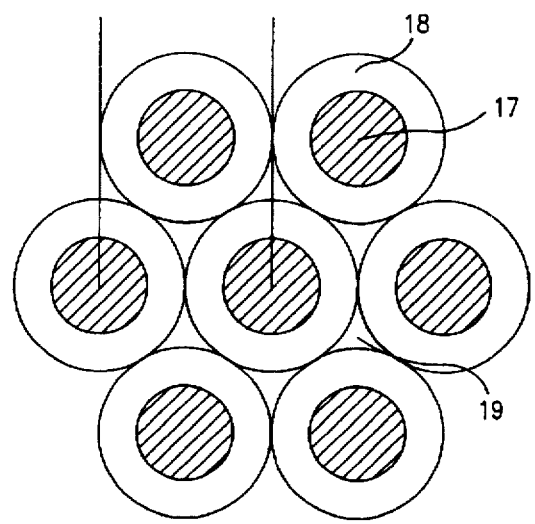

FIG. 2 is a fragmentary cross section illustrating a fiber optic bundle in an endoscope.

Figure 3:
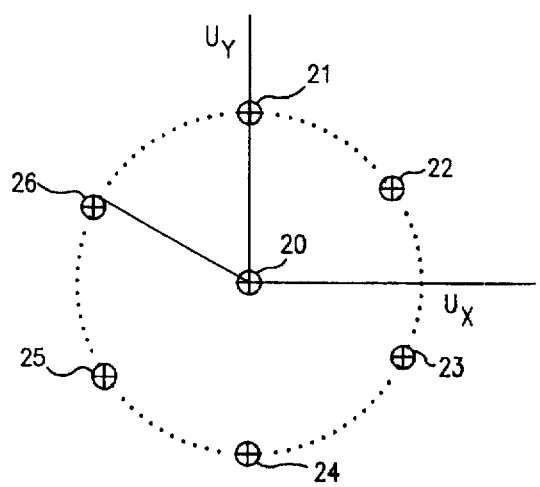

FIG. 3 is a diagram illustrating first order spatial frequencies in a sampling of a spectrum of fiber optic bundles.

Figure 4:
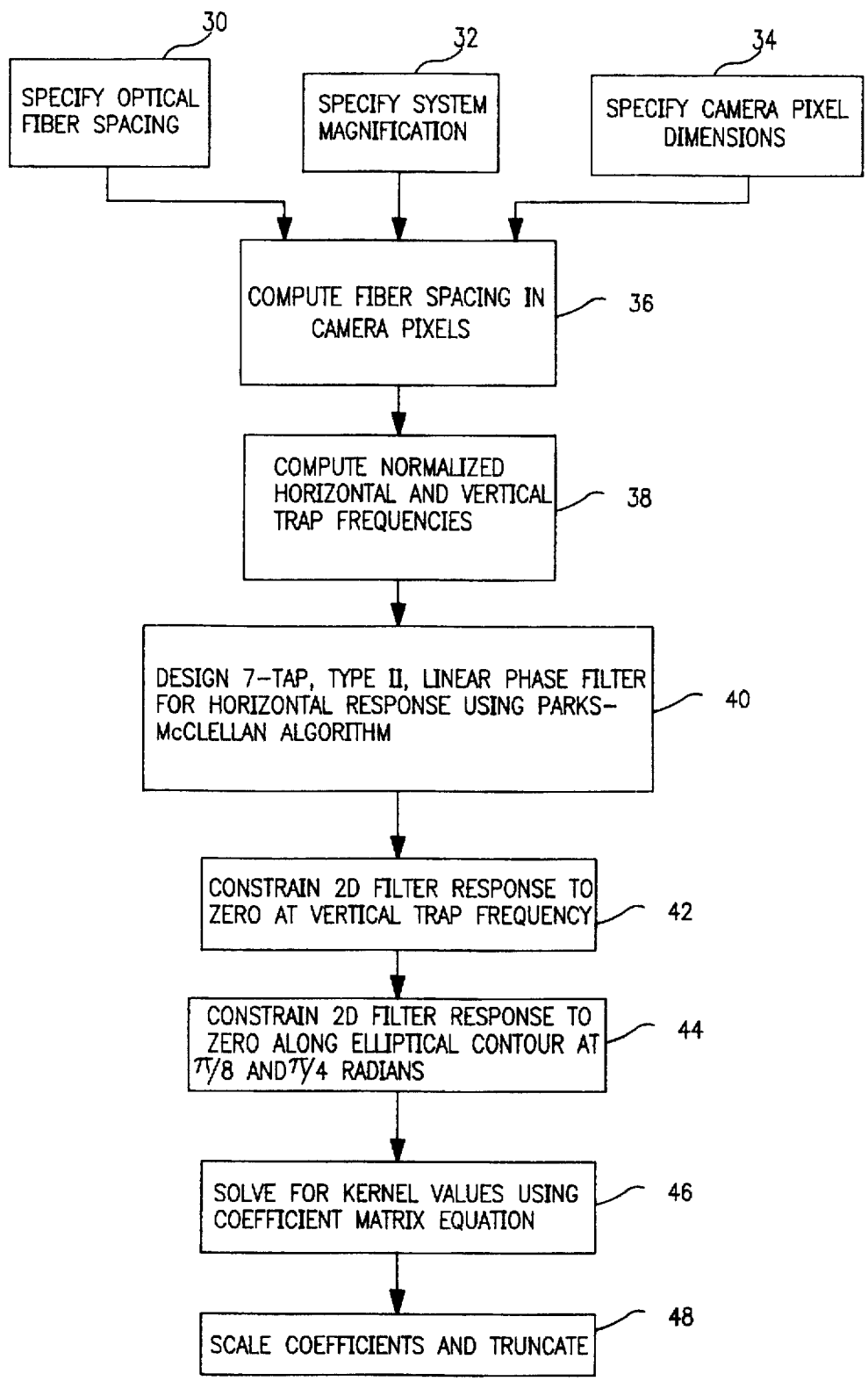

FIG. 4 is a flow diagram illustrating the design of a linear filter for removing the grid pattern from an image.

Figure 5:
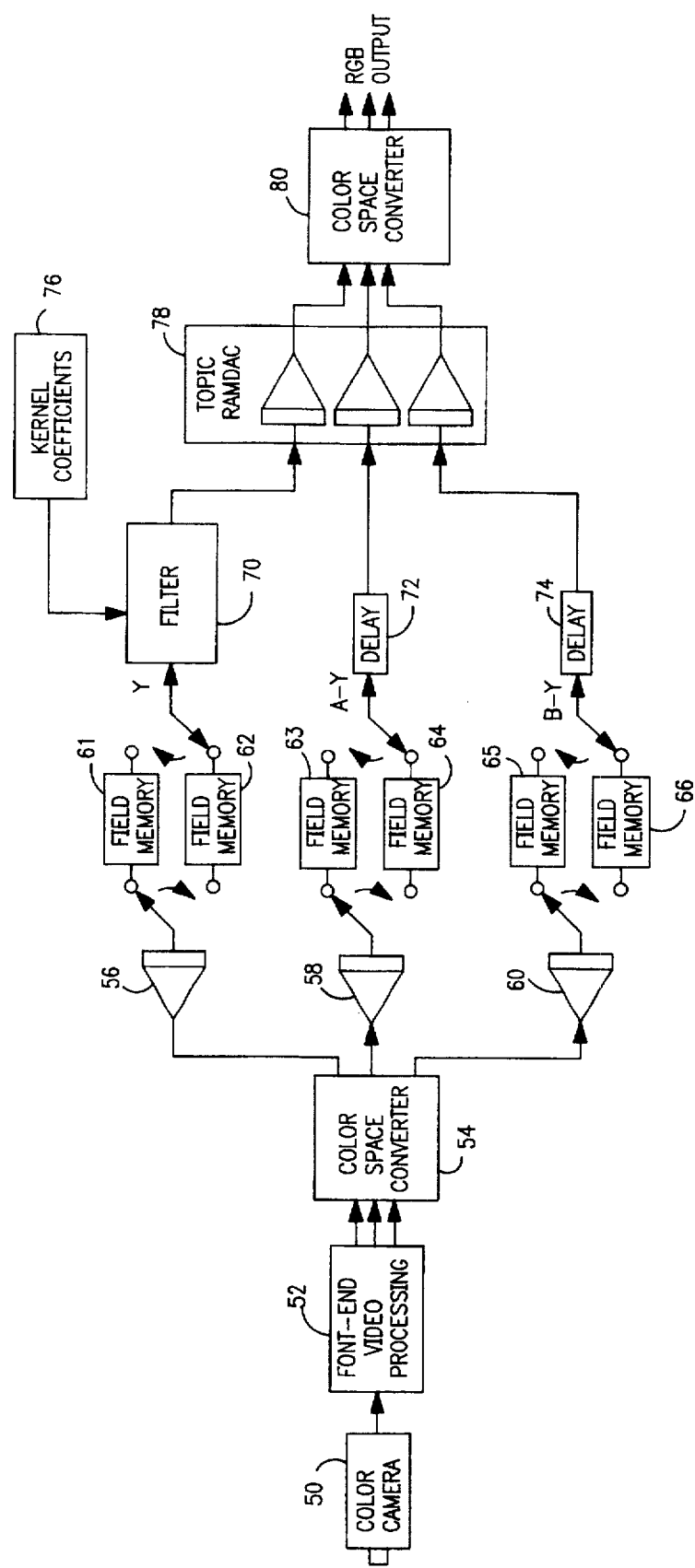

FIG. 5 is a block diagram of a basic system using the linear filter design of FIG. 4.

Figure 6:
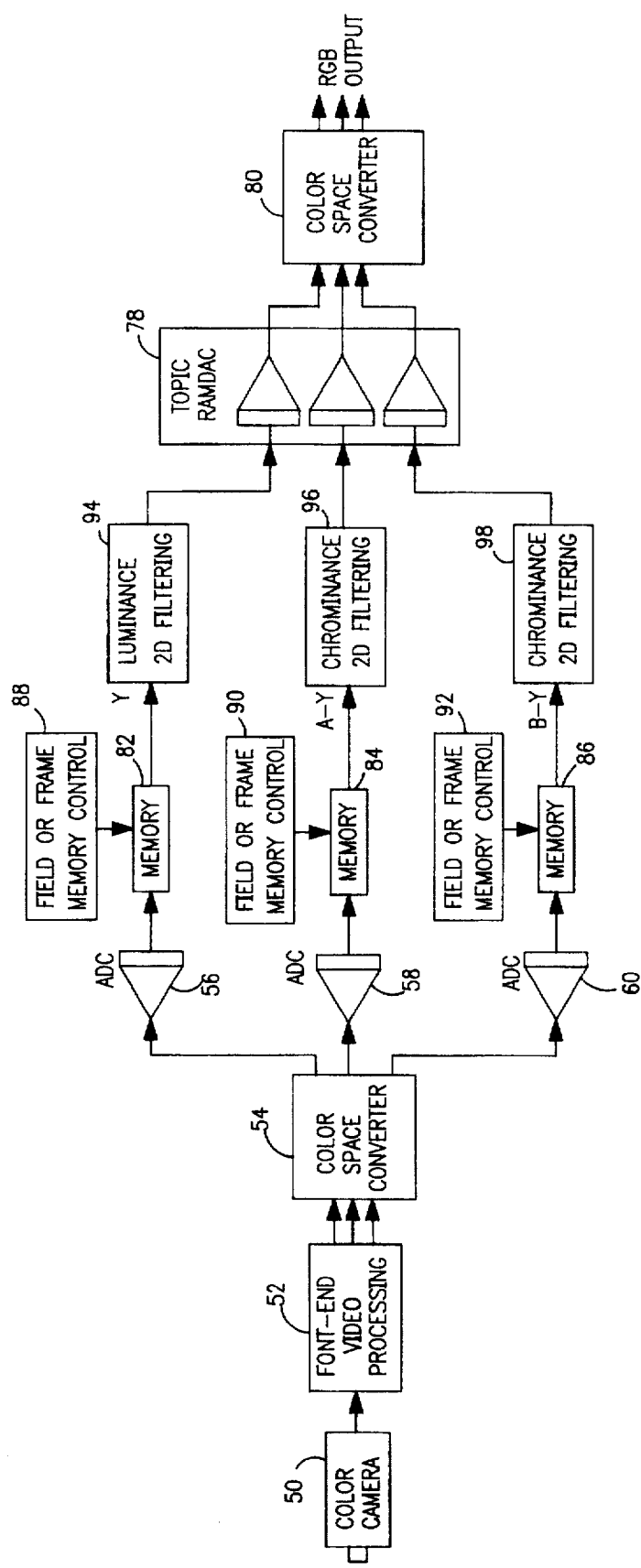

FIG. 6 is a schematic block diagram of a sophisticated system for filtering the image of a high resolution camera for removing the grid pattern.

Figure 7:
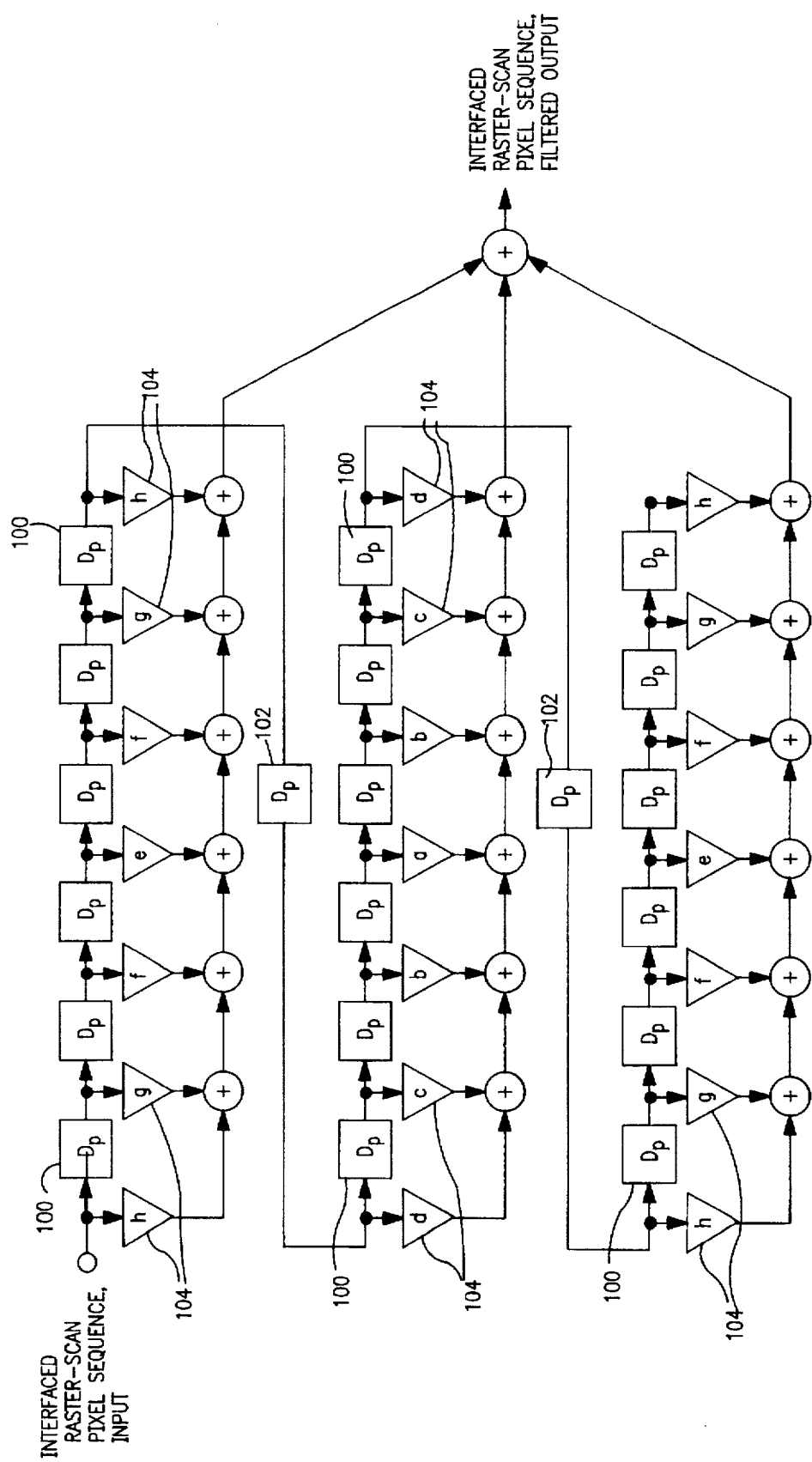

FIG. 7 is a block diagram of the filter processing of a convolver used in the invention.

Figure 8:
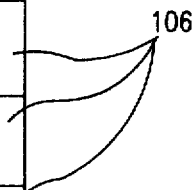

FIG. 8 is a table of the kernel coefficients, field mode for use in development of the linear filter according to the invention.

Figure 9:
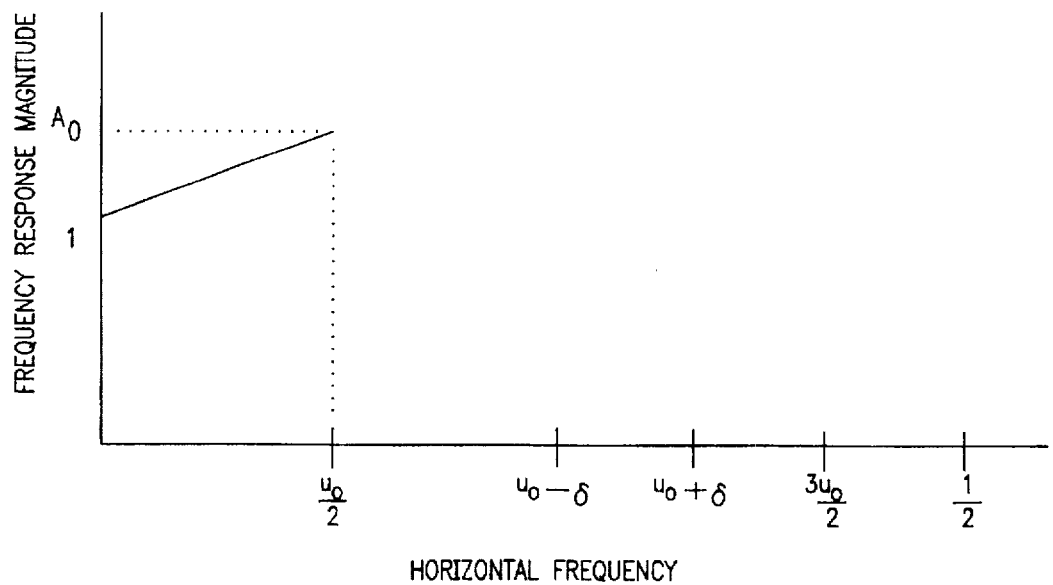

FIG. 9 is a graph of the desired horizontal frequency response function.

Figure 10:
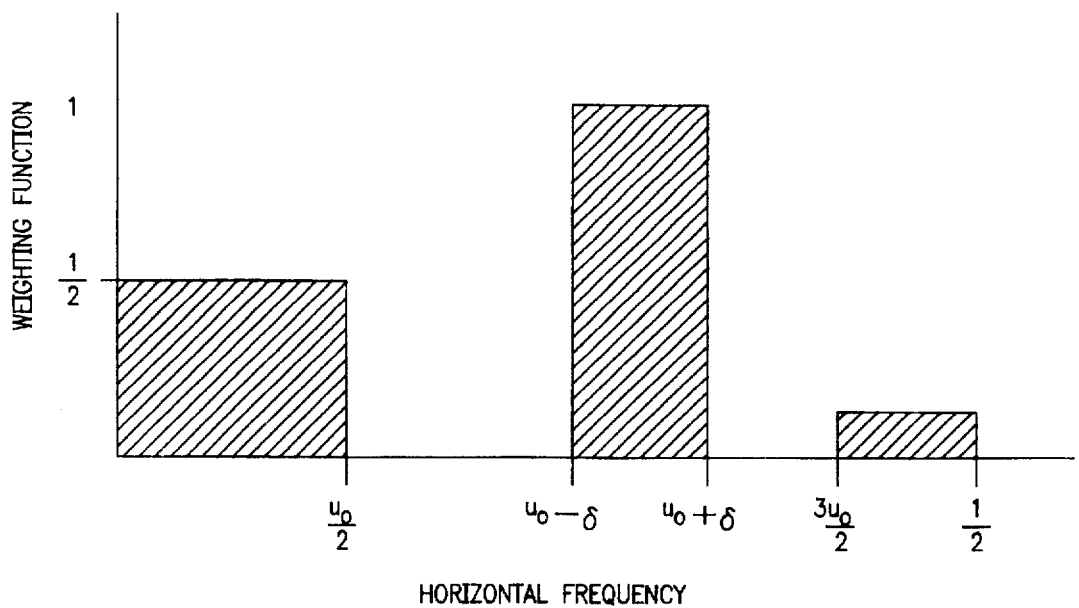

FIG. 10 is a graph of the weighting function associated with the target response bands.

DETAILED DESCRIPTION OF THE INVENTION

The fiber optic portion 10 of an endoscope is shown in FIG. 1. The details of a complete endoscope are not given, because they are not important to an understanding of the invention. Suffice it to say that it will include structural surrounding support, such as a rigid tube for a rigid endoscope, or a flexible sheath for a flexible endoscope. This surrounding structure for a flexible endoscope encloses, among other items, a fiber optic bundle 11, an objective lens 12 and an ocular lens 13, which are schematically shown. The image is focused on a camera 14 such as a CCD. The signal from the CCD is processed in a processor 15 (to be described), and then is provided to the user on a video display 16.

FIG. 2 is a fragmentary cross-section showing only an illustrative seven of the circularly-sectioned fibers which form the bundle. Each fiber has a central core 17 for transmission of light. Each core is surrounded and embraced by a peripheral cladding 18, which may comprise one or more layers. The cladding material does not transmit light for an image. Such fibers will nest together to form interstices 19. These interstices are generally triangularly shaped. Also the interstices, between adjacent fibers, do not transmit light for an image.

In turn, the fibers typically nest so that each fiber is contacted by six neighboring fibers. As a consequence, the combined claddings and interstices form a generally hexagonal dark pattern in the transmitted image, the core areas being disposed in a generally hexagonal pattern.

Because light is not transmitted through the claddings and interstices, a dark grid results throughout the image. The elimination of this dark pattern will be sufficient to improve the image for many purposes, because the resulting pattern will be a darker color, at least. Optionally, a color and intensity approximating of neighboring fiber cores may be supplied.

In one embodiment of the invention, which when analyzed in the spatial frequency domain, a linear digital filter attenuates certain key frequencies which compose the interstitial pattern. When analyzed in the spatial domain, the linear filter utilizes neighboring pixels to interpolate image information into the interstitial region.

With reference to the configuration shown in FIG. 2, FIG. 3 shows the DC and first order frequencies in the fiber sampling spectrum. The DC component 20 is at the center. Six first-order frequencies 21–26 are shown equally spaced from one another, located on a circle whose radius is:

$$\frac{2\sqrt{3}}{3} \frac{1}{d_f}$$

where $d_f$ is the mean fiber spacing.

Higher order frequencies do exist, but for purposes of this invention they may be ignored. This is because the first-order frequencies comprise most of the energy in the interstitial pattern.

The key to reducing interstitial grid pattern is to attenuate amplitudes of the first order spectral components. The linear digital filter, conceived and described herein, performs this function by acting as a trap to increase the gain and attenuate those first order spatial frequency components that contribute most to this interstitial grid pattern.

A problem with the image produced, is that the fiberscope spectrum at the image is affected by optical magnification typically controlled by the user and usually not known by the camera processor. Magnification variations alter the location of the first order spectral components and therefore, compromise the performance of a fixed filter design. For this reason, filters can be provided, which span a range of probable filter spacings and optical magnifications. Optimum filters can be selected automatically by appropriate algorithms.

The filtering system of the present invention works well because it employs relatively small kernels which are optimized for a specific fiber spacing. The system of the present invention works on a low level to provide a more sophisticated correction for the grid pattern. The grid formed by the interstitial pattern, between respective cores in the fiber optic bundle, represent frequencies that can be filtered out. Thus, the system of the present invention is a filtering system that can provide incremental image correction pixel by pixel. FIG. 4 is a flow diagram illustrating the preferred design of a filter for use in the system to filter out the interstitial grid pattern.

A design method for producing a filter, uses a 3×7 element (i.e., 3 elements vertical, 7 elements horizontal, 21 elements total) kernel, and is shown in the flow diagram of FIG. 4. The first step is to specify the optical fiber spacing 30 ($d_f$), system magnification 32, (M) and video processing horizontal ($T_h$) and vertical ($T_v$) pixel dimensions of camera 34. From this, the spacing of the camera pixels is computed 36. That is the horizontal ($d_h$) and vertical ($d_v$) fiber spacing in the processing pixels is computed from:

$$d_h = d_f \frac{M}{T_h}$$

and $$d_v = d_f \frac{M}{T_v}$$

The fiber spacing is then used to compute the normalized horizontal and vertical trap frequencies 38 ($u_0, v_0$) from:

$$u_0 = \frac{2\sqrt{3}}{6} \frac{1}{d}$$

$$v_0 = \frac{2\sqrt{3}}{6} \frac{1}{d}$$

The horizontal response is then determined using Parks-McClellan algorithm 40 to design a 7-tap, Type II linear phase filter. This algorithm requires a piecewise linear target frequency response function and weighting function. The target frequency response and weighting functions are shown in FIGS. 9 and 10.

The bold lines in FIG. 9 define the desired magnitude response bands. Transition bands lie between the desired response bands. The result of this design is a sequence of coefficients as shown below. Coefficient $a_0$ is the zero delay element.

$$h[n] = \{d_0, c_0, a_0, c_0, d_0\}$$

The two dimensional filter response is then constrained to zero (0) at the vertical trap frequency 42. This means the frequency response function, $H(u,v)$ is constrained to zero at $V_0$, i.e., $H(0,v_0)=0$.

The frequency response is then constrained to zero at points $\pi/8$ and $\pi/4$ along the elliptical contour 44. The frequency response function is constrained to zero according to:

$$H(u_0 \cos(\pi/8), v_0 \sin(\pi/8)) = 0$$

$$H(u_0 \cos(\pi/4), v_0 \sin(\pi/4)) = 0$$

Kernel values will then be solved for using a coefficient matrix equation 46. The kernel coefficients are solved for using the matrix equation:

$$h_s = A^{-1} b,$$

where, $$A = \begin{bmatrix} A_1 \\ A_2 \end{bmatrix}$$

$$A_1 = \begin{bmatrix} 1 & 0 & 0 & 0 & 2 & 0 & 0 & 0 \\ 0 & 2 & 0 & 0 & 0 & 4 & 0 & 0 \\ 0 & 0 & 2 & 0 & 0 & 0 & 4 & 0 \\ 0 & 0 & 0 & 2 & 0 & 0 & 0 & 4 \\ 1 & 2 & 2 & 2 & 0 & 0 & 0 & 0 \end{bmatrix}$$

$$A_2 = \begin{bmatrix} 1 & 2\cos(2\pi u_1) & 2\cos(4\pi u_1) & 2\cos(6\pi u_1) & 2\cos(4\pi v_1) & 4\cos(2\pi u_1)\cos(4\pi v_1) & 4\cos(4\pi u_1)\cos(4\pi v_1) & 4\cos(6\pi u_1)\cos(4\pi v_1) \\ 1 & 2\cos(2\pi u_2) & 2\cos(4\pi u_2) & 2\cos(6\pi u_2) & 2\cos(4\pi v_2) & 4\cos(2\pi u_2)\cos(4\pi v_2) & 4\cos(4\pi u_2)\cos(4\pi v_2) & 4\cos(6\pi u_2)\cos(4\pi v_2) \\ 1 & 2\cos(2\pi u_3) & 2\cos(4\pi u_3) & 2\cos(6\pi u_3) & 2\cos(4\pi v_3) & 4\cos(2\pi u_3)\cos(4\pi v_3) & 4\cos(4\pi u_3)\cos(4\pi v_3) & 4\cos(6\pi u_3)\cos(4\pi v_3) \end{bmatrix}$$

$(u_1,v_1) = (\cos(\pi/8), \sin(\pi/8))$, $(u_2,v_2) = (\cos(\pi/4), \sin(\pi/4))$, and $(u_3,v_3) = (1/2, 1/4)$, i.e., $H(u_1,v_1) = H(u_2,v_2) = H(u_3,v_3) = 0.$ $$b = \left( a_o \; 2b_o \; 2c_o \; 2d_o \; \frac{\cos(4\pi v_o)}{\cos(4\pi v_o) - 1} \; 0 \; 0 \; 0 \right)^T$$

$h_3 = (a \; b \; c \; d \; e \; f \; g \; h)^T$.

48. The convolver coefficients are multiplied by a factor $\alpha$ bounded by $$1 \leq \alpha \leq \frac{\sqrt{3}}{2} \cdot \frac{d_f}{a_c}$$

where $d_f$ is the fiber spacing and $a_c$ is the fiber core radius. Round the scaled coefficients to signed, 8 bit fixed-length.

A linear digital filter, designed by the method shown in the flow diagram of FIG. 4, is then used to filter out the interstitial grid pattern in the basic system shown in FIG. 5. Color camera 50 receives an image through fiber optic bundle 10 (FIG. 1) and delivers it to a video processor 52 and color space converter 54. Typical color converters process luminance (Y), chroma (G-Y), chroma (B-Y), red, green, blue lines, hues, etc. The output of color space converter 54 is then converted to digital by flash analog to digital (ADC) converters 58 and 60. The digital signal is alternately delivered to field memories 61 through 66. While one image is delivered to field memories 61, 63 and 65 the other field mode image from field memories 62, 64 and 66 is being processed by the image processing filter 70, delay 72 and delay 74 as will be described in greater detail hereinafter. In the basic system shown in FIG. 5, only the luminance signal (Y) need be processed to reduce the grid pattern. In a basic system (single chip CCD), the chrominance signals are of low spatial resolution, and the grid pattern is less intrusive than in a luminance color plane.

Preferably, filter 70 is a convolver which receives kernel coefficients 26 for convolution processing and delivers the filtered output to a triple random access memory digital to analog converter 78. The signal is then processed by color space converter 80 for output as a RGB signal.

A more sophisticated system is illustrated in FIG. 6 for working in a field or a frame mode. The system receives input from endoscope 10 (FIG. 1) to camera 50 for processing by video processor 52, color space converter 54 and flash analog to digital converters 56, 58 and 60 as before. The output of the analog to digital converters is then delivered to memory 82, 84 and 86 under field or frame control 88, 90 and 92 respectively.

The system shown in FIG. 6 is for a color image processing system that has high resolution color (for example, a three chip CCD). For this reason, image improving filtering is needed in both the luminance and the chroma signals and is provided by luminance filter 94 and chrominance filters 96 and 98 or any other color representation. As before, the filtered signal is output to a triple RAM digital to analog converter 78 for processing by color space converter 80 to provide a RGB output.

The filters used in the systems described in FIGS. 5 and 6 can be any filter designed according to the process described with respect to FIG. 4, or any other method which maximizes attenuation at the frequencies shown in FIG. 3. However, the filter is preferably a Convolver such as a Model No. IMSA110 Convolver, manufactured by SGS-Thompson Microelectronics configured as a 3×7 element field mode convolver, as illustrated in FIG. 7.

The convolver, configured as a linear digital filter, receives interlaced raster scan pixel sequence input as shown in FIG. 7. The pixels in the sequence are sequentially multiplied by a respective coefficient, delayed, multiplied by the next coefficient then summed with the previous product and so on until processed by all coefficients a through h. $D_p$ represents pixel delays, while $D_h$ represents a horizontal line delay of the 3×7 element kernel. The output is the sum of the sequential multiplication by the coefficients represented by the kernel coefficient notation in the table of FIG. 8 and summing of all the products. Each coefficient in the pixel processing sequence in the convolver corresponds to a coefficient of elements 106 shown in the table of FIG. 8. The filtering kernel represented by FIG. 8 measures three elements vertical by seven elements horizontal, and has twenty-one elements total. Thus, the selected kernel convolver has eighteen pixel delays 100 ($D_p$), two horizontal line delays 102 ($D_h$) and twenty-one coefficient multipliers 104 (a through h) to provide an output which is the sum of all products.

The composite signal output of the system, using the filter technique shown, substantially eliminates the interstitial grid pattern between respective pixels and improves the overall brightness of the image. The system shown improves image brightness without requiring a brighter light source, thereby protecting sensitive tissue from potential heat generation at the tip of an endoscope.

The system also comprehends a process for improving image by a dilation process using a domain. The dilation process is a non-linear image processing algorithm, which replaces each pixel with a maximum pixel brightness of a pixel in the immediate neighborhood depending on the domain of the dilation kernel chosen. The dimensions of the neighborhood are defined by the domain of the dilation kernel. The dilation process is applied to all pixels in the image except those at the edges where the dilation kernel neighborhood lies outside the image domain. The processing algorithm for replacing each pixel with a maximum pixel brightness on a nearby pixel for example is:

$$g_{i,j} = max( \ldots, K_{-1,-1}f_{i-1,j-1}, K_{-1,0}f_{i-1,j}, \ldots, K_{0,0}f_{i,j}, \ldots, K_{1,1}f_{i+1,j+1}, \ldots ),$$

where $f_{i,j}$ and $g_{i,j}$ denote pixels in the input and output images of the dilation process, respectively, and integers i and j are horizontal and vertical indices. The elements of the dilation kernel are denoted by $K_{i,j}$. A typical kernel has 3(V)×3(H) elements with each element in the kernel having value one. Other dilation kernels can be used depending upon image magnification, fiber spacing and fiber core to fiber spacing ratio.

The kernel selection for the dilation process used to reduce the grid of a flexible endoscope image for fixed magnification is determined by the following steps.

1. Determine the number of detector (CCD) pixels, which fit in the space between adjacent fibers in a bundle in the horizontal (M) and vertical direction (N); a typical example of four to five CCD pixels fitting between the vertical and horizontal core separations (grid) of a fiber bundle have been found; i.e., M=N=4;

2. Select a matrix size (M+2)×(N+2);

3. Set all kernel coefficients used for the dilation process to one; i.e., Ki,j=1 for i=1, . . . M+2, j=1, . . . N+2.

Using the process described, an image is observed from a real-time image processing system where the dilation process can provide the filtering 94,96 and 98 in FIG. 6. That is by replacing the convolver with a rank value filter. With the dilation processing as described, there should be no grid visible. However, if the grid is still visible, M and N can be increased accordingly until all the grid is removed.

In principle, all combinations of on/off dilation kernel coefficients could be tried until one is found which gives the best overall image improvement (i.e., reduced grid) increased image brightness and no loss of spatial resolution. Typically, however, the system is symmetric and as a start, all four corner dilation kernel coefficients [i,j=(0,0), (0,N), (M,0), (M,N)] can be set to 0 leaving all other coefficients at 1. By continuing this process, the best dilation kernel is determined for the given magnification. The process can be stopped when no crosstalk is obtained; that is, the information from one fiber core is not transmitted into any area of another fiber core. The more regular the fiber spacing, the better the process functions.

The dilation process described above expands the brightness of pixels and can be combined with other processes to further improve the endoscope image. The dilation process itself could be a secondary process to the filtering process described hereinabove. Alternatively it could be a combined with a secondary process being a second dilation using the same or a different kernel, or the filtering process described above with smoothing or any combination thereof to further improve the image appearance depending upon the type of information viewed (spatial frequency or color content of the image). The optimum number of steps, kernel size and configuration depends upon the fiber optic image bundle, the optical system magnification and the CCD pixel pattern.

Secondary processes can bring some of the image back to optimum visualization of such acquired and processed images depending upon the application of the class of images and use of such an instrument. For example, if the instrument is used to display biological tissues with surgical instruments visualizing a minimal invasive surgical procedure.

The dilation process described above is well suited to CCD cameras, which are detachable from a flexible fiber optic endoscope since the relationship between the CCD pixel matrix and the image bundle matrix is not relevant for the process to work.

This invention is not to be limited by the embodiments shown in the drawings and described in the description which are given by way of example and not of limitation, but only in accordance with the scope of the appended claims.

What is claimed is:

1. In combination with an endoscope and a video display, said video display having an array of pixels for displaying purposes, said endoscope including an objective lens at its distal end and a fiber optic bundle for transmitting an image to a CCD camera at it proximal end;

said fiber optic bundle comprising a substantial number of optical fibers each with distal and proximal ends, the ends of said fibers forming an array which is identical at both of said ends of said bundle, whereby to forward an image from said lens to said camera, each said fiber consisting of a central light-transmitting core and a peripheral cladding, said fibers being clustered so as to form voids between groups of contacting fibers, said claddings and said voids being non-transmissive of light so as to form a visible dark grid encompassing said light-transmissive cores;

said camera having arrays of pixels at photo sites on said camera respective to pixels on said display, the improvement comprising;

grid reduction means receiving pixel signals from said camera and generating respective enhanced signals for said display, said grid reduction means comprising circuitry which adjusts the color and intensity of the signal generated by the CCD respective to pixels in said grid, thereby to reduce the prominence of said grid.

2. Apparatus according to claim 1 in which said circuit means adjusts the output signal of each camera pixel as a function of the color and intensity of at least some near neighboring camera pixels.

3. Apparatus according to claim 2 in which the intensity of the signal received from the camera is adjusted to the color and intensity of the most intense one of a group of nearby camera pixels.

4. Apparatus according to claim 3 in which said group of nearby covered pixels comprises a matrix array of surrounding camera pixels of a rectangular array including said respective pixel.

5. Apparatus according to claim 3 in which said matrix array is a symmetric matrix array which includes said respective pixel.

6. Apparatus according to claim 1 in which said circuit means comprises filter means which alternates the frequency components of the spatial frequencies which comprise the grid pattern.

7. Apparatus according to claim 6 in which said filter means comprises a convolver which multiplies the respective pixels in a sequence by respective stored values and sums the multiplied outputs to uniformly increase the intensity of respective pixels in said sequence thereby attenuating said grid pattern.

8. Apparatus according to claim 7 in which said respective stored values are coefficients of values in a kernel.

9. Apparatus according to claim 8 in which said kernel is a 3×7 stage array.

10. Apparatus according to claim 9 in which each pixel is multiplied by a coefficient derived from each stage in said array and added to the output of a previous stage and summed at an output.

11. Apparatus according to claim 10 in which said kernel is shafted a predetermined amount often processing each pixel sequence.

12. Apparatus according to claim 11 in which said filter means filters the luminance signal.

13. Apparatus according to claim 11 in which said filter means comprises a filter in the luminance channel and in both chroma channels or in red, green, blue channels.

14. Apparatus according to claim 13 including field and frame memory control means for controlling the field mode or frame mode input to said filter means.

15. A method of improving an endoscope image received through a fiber optic bundle to remove said interstitial grid pattern comprising;

converting said endoscope image to a digital image signal;

processing said digital image signal to generate respective enhanced pixel signals;

converting said processed digital signal image to a switchable color output signal;

whereby said interstitial grid pattern is substantially removed.

16. The method according to claim 15 in which said processing comprises linear digital filtering of said digital image to remove the spatial frequencies composing said interstitial grid pattern.

17. The method according to claim 16 in which said linear digital filtering comprises; selecting a kernel having predetermined elements from a ratio of the pixel to fiber spacing of said fiber optic bundle; calculating the coefficient of the elements in said kernel; sequentially multiplying the pixels in said digital image by each of said coefficients in said kernel and summing said multiplied values whereby relative pixel brightness is enhanced and said interstitial pattern is substantially valued.

18. The method according to claim 17 including selecting 3×7 element kernel.

19. The method according to claim 18 in which each pixel is sequentially multiplied by each coefficient, added to the value of the previous multiplied pixel and summed at the output.

20. The method according to claim 16 in which said linear digital filtering comprises processing said digital image in a convolver.

21. The method according to claim 20 comprising processing only the luminance signal.

22. The method according to claim 15 comprising dilating respective pixels in said digital image signal to improve the overall brightness and substantially eliminate the interstitial grid pattern.

23. The method according to claim 22 comprising dilating respective pixels by replacing each pixel with the maximum pixel brightness of a pixel in the immediate neighborhood.

24. The method according to claim 23 comprises selecting a kernel of pixels; processing each pixel of said kernel in an image processing algorithm.

25. The method according to claim 24 comprising selecting an optimum kernel by determining the ratio of detector pixels to the space between fiber cores of said fiber optic bundle; select a matrix size relative to said ratio; set all coefficients of said kernel used for dilation to one; whereby said image processing algorithm replaces the brightness of each pixel with the brightness of a nearby brightest pixel in said kernel domain.

26. The method according to claim 25 in which said selected kernel domain is a symmetric matrix.

27. The method according to claim 26 in which said symmetric matrix is between 3×3 and 6×6 symmetric matrix.

* * * * *